United States Patent [19]

Asche et al.

[11] Patent Number: 5,122,140
[45] Date of Patent: Jun. 16, 1992

[54] DYNAMIC EXTERNAL FIXATION DEVICE

[75] Inventors: Gernot Asche, Freudenstadt, Fed. Rep. of Germany; Marcel H. Wagenknecht, Le Lignon, Switzerland

[73] Assignee: Jaquet Orthopédie, S.A., Geneva, Switzerland

[21] Appl. No.: 572,523

[22] Filed: Aug. 23, 1990

[51] Int. Cl.[5] .................................. A61F 5/04
[52] U.S. Cl. ........................ 606/55; 606/57; 606/59
[58] Field of Search ........................ 606/53–59

[56] References Cited

U.S. PATENT DOCUMENTS

| | | | |
|---|---|---|---|
| 4,273,116 | 6/1981 | Chiquet | 606/59 |
| 4,488,542 | 12/1984 | Helland | 128/84 B |
| 4,628,919 | 12/1986 | Clyburn | 606/55 |
| 4,628,922 | 12/1986 | Dewar | 606/59 |
| 4,848,368 | 7/1989 | Kronner | 606/57 |
| 4,988,349 | 1/1991 | Pennig | 606/57 |
| 5,019,077 | 5/1991 | De Bastiani | 606/57 |

Primary Examiner—Robert A. Hafer
Assistant Examiner—Michael Brown
Attorney, Agent, or Firm—Peter C. Richardson; Lawrence C. Akers; Elizabeth O. Slade

[57] ABSTRACT

This dynamic external fixation device for the wrist comprises an articulated joint 10 arranged between assemblies 40 and 50 for fixation of groups of pins 60 and 70 inserted in the bone on either side of the articulation 80 whose axis is detected by means of targeting needles 90. The fixation assemblies 40 and 50 permit positioning of the fixation device in the plane of the arrows A and B, while an adjustment device 20 and a device 30 permitting play permit its inclination transversely relative to this plane, without disturbing the positioning previously obtained.

18 Claims, 4 Drawing Sheets

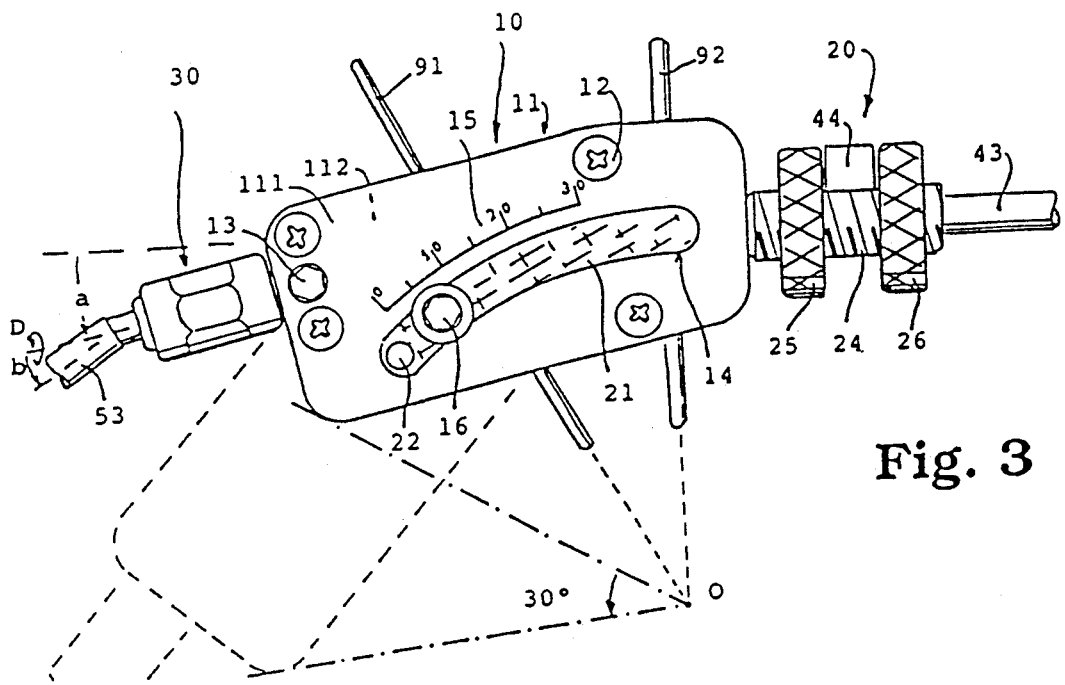
Fig. 3
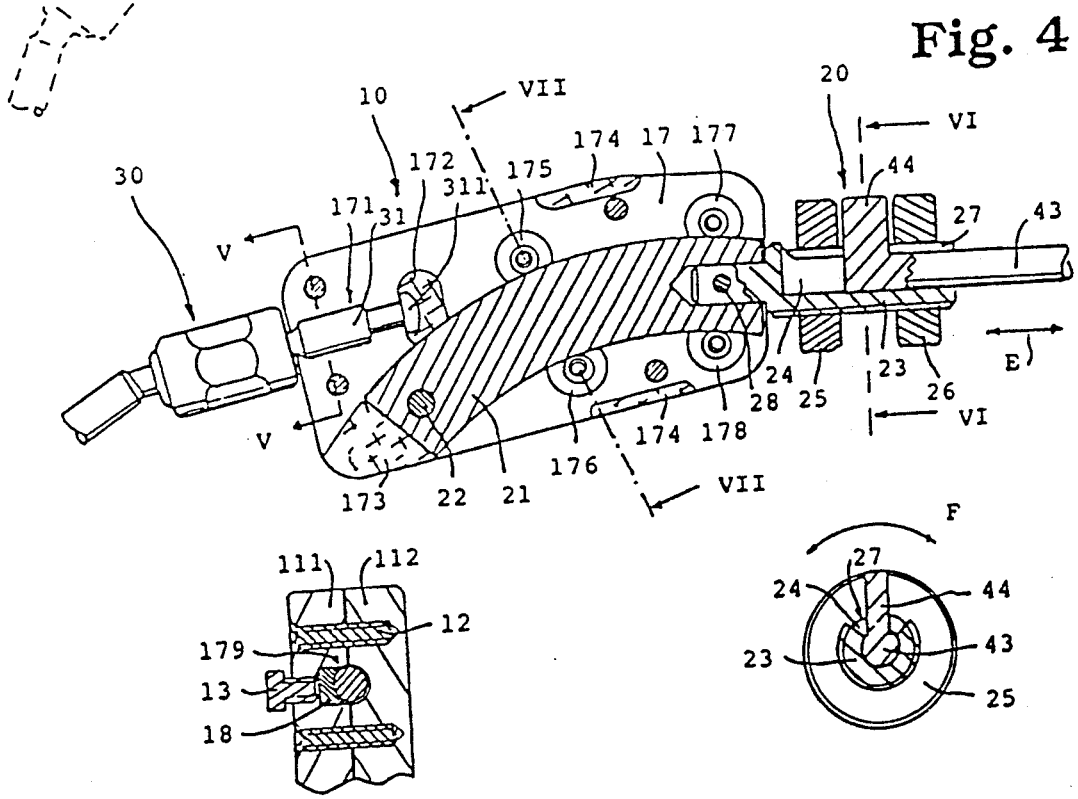
Fig. 4
Fig. 5
Fig. 6

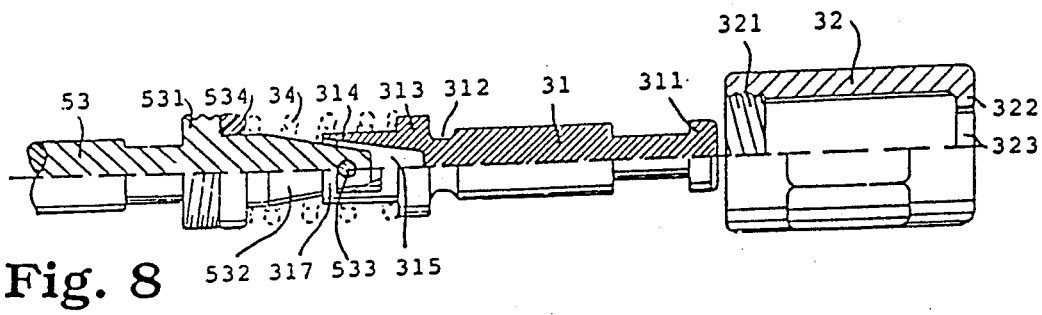
Fig. 8
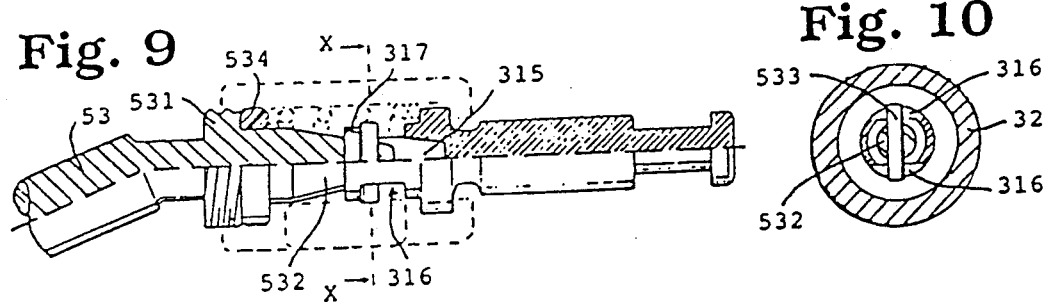
Fig. 9
Fig. 10
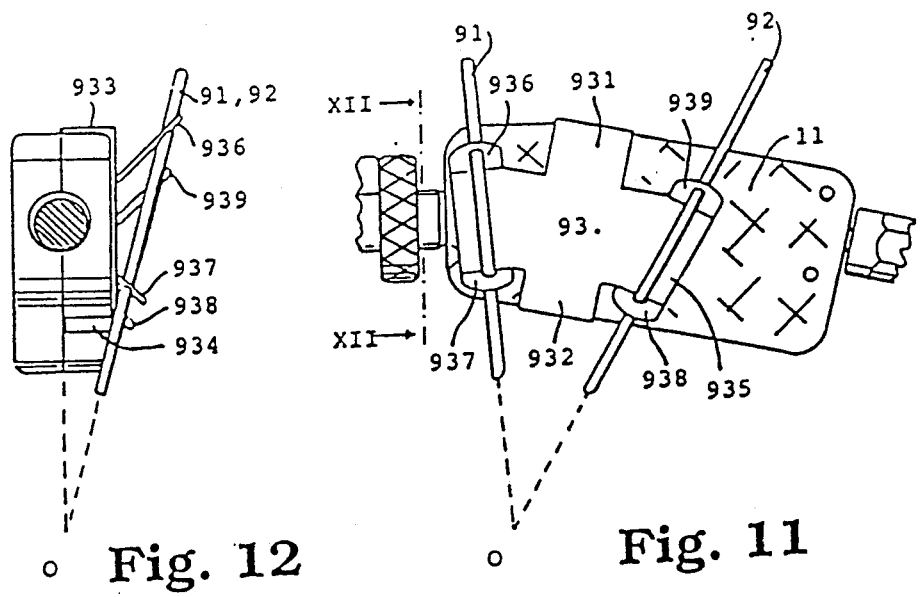
Fig. 12
Fig. 11

DYNAMIC EXTERNAL FIXATION DEVICE

The present invention is in the field of medical equipment and relates more particularly to a dynamic external fixation device for the wrist.

For some years it has been known that one secondary effect of immobilizing a fractured bone in the vicinity of an articulation is a numbing of the articulation, which often necessitates a long re-education. A technique has therefore been developed using pins which are inserted in the bone, on either side of the fracture, and which are connected by a fixation device comprising an articulated joint permitting, under medical supervision, a natural movement of the articulation.

For example, in the case of fractures in the distal part of the radius, the external fixation device must be able to permit a natural movement of the wrist, a movement whose extent can be increased in the course of the osseous consolidation. In this case, the pins are inserted, on one side, into the radius and, on the other side, into the metacarpus.

It is necessary for the fixation device to follow the natural movement of the articulation, and it must therefore be possible for it to be adjusted relative to the anatomical movement of the wrist, in order to prevent any dislocation of the fracture.

U.S. Pat. No. 4,628,919 (Clyburn) already discloses a fixation device intended to be worn on the inner side of the forearm and comprising a rear branch and a front branch connected via a ball joint, each branch serving for the fixation of pins. The front branch additionally makes it possible to effect a controlled elongation or contraction. Moreover, the ball joint comprises means for regulating the degree of relative movement between the rear and front branches.

It has been found that it is preferable, during the course of the consolidation, to limit the movement of the wrist to a flexion movement of the hand relative to the forearm, rather than to permit omnidirectional movement of the hand.

To this end, the Applicant has already proposed, in European Patent . . . (publication no. 0,248,138), a dynamic external fixation device for osteosynthesis of a fractured articulation, comprising a first member having a fixation rod capable of being connected to pins inserted in the bone on one side of the articulation; a second member having a fixation rod capable of being connected to pins inserted in a bone on the other side of the articulation; and an articulated joint connecting these two members, which has a curved sliding surface possessing a virtual axis, this articulated joint comprising means for targeting the axis of the sliding surface.

It has been found that it is not sufficient to make the axis of the sliding surface coincide with the center of the articulation and that it is furthermore necessary to be able to incline the articulated joint transversely relative to the longitudinal axis of the apparatus, but without disturbing the latter, in order to be able to adapt the fixation device more precisely to the anatomy of the patient.

The present invention consequently relates to a dynamic external fixation device for osteosynthesis of a fractured articulation, comprising:
a first member having a fixation rod capable of being connected to pins inserted in the bone on one side of the articulation;
a second member having a fixation rod capable of being connected to pins inserted in a bone on the other side of the articulation;
and an articulated joint connecting the rods, which has a curved sliding surface having a virtual axis, the said articulated joint comprising means for targeting the said axis of the sliding surface.

This fixation device is characterized by the fact that the articulated joint comprises a casing having the said sliding surface and an arc-shaped segment capable of sliding on the said surface, and by the fact that at least one of the said rods is capable of pivoting on its axis relative to the casing in order to permit the transverse positioning of the articulated joint without affecting the longitudinal adjustment.

In a preferential variant, the external fixation device additionally comprises a device permitting one of the fixation rods some play relative to the articulated joint.

The attached drawings represent, by way of non-limiting examples, some embodiments of the subject of the present invention.

FIG. 3 is a side view of the device in FIG. 1, from the opposite side, showing the maximum extent of the movement permitted.

FIG. 4 is a longitudinal section of the elements in FIG. 3.

FIG. 5 is a cross-section along V—V in FIG. 4, showing the locking of the angular adjustment of the front part.

FIG. 6 is a cross-section along VI—VI in FIG. 4, showing the components constituting the angular adjustment of the rear part.

FIG. 8 shows in detail the components constituting the angular adjustment of the front part, seen from above in the lower half of the drawing and in section in the upper part.

FIG. 9 is a view similar to that in FIG. 8, the components being seen from the side in the lower half of the drawing and in section in the upper part.

FIG. 10 is a cross-section along X—X in FIG. 9.

FIG. 11 is a side view of a removable device for guiding the targeting needles.

FIG. 12 is a cross-section along XII—XII in FIG. 11.

Figure 1:
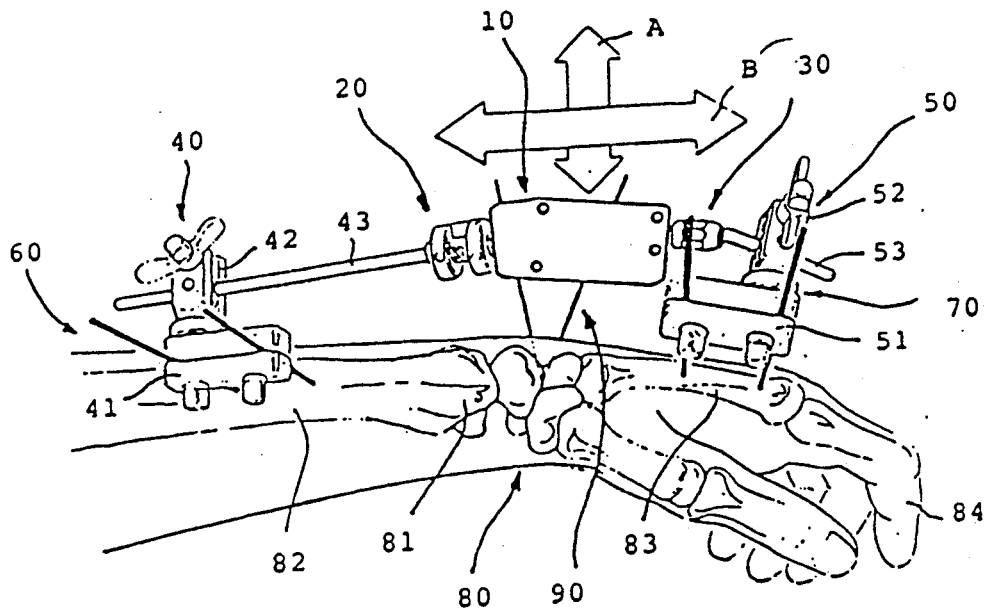
FIG. 1 is a side view of a wrist on which there is arranged a dynamic external fixation device according to the invention.
Figure 2:
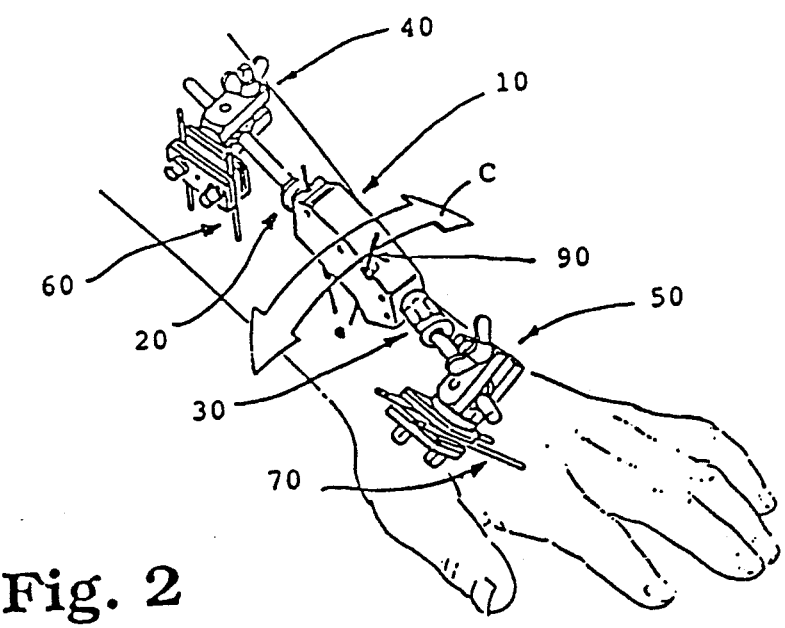
FIG. 2 is a plan view of the assembly in FIG. 1.

In the representation in FIGS. 1 and 2, the dynamic external fixation device according to the invention consists of an articulated joint 10 arranged between an adjustment device 20 and a device 30 permitting play.

The devices 20 and 30 are integral, respectively, with a rear assembly 40 and a front assembly 50 for fixation of pins 60 and 70 inserted in the bones on either side of an articulation 80. Needles 90, integral with the articulated joint 10, make it possible to target the central point of the articulation 80.

The rear and front assemblies 40 and 50 consist, in a conventional manner, of pin-holders 41 and 51, respectively, which can be oriented relative to a positioning and locking flange 42, 52 on a fixation rod 43, 53 integral, respectively, with the devices 20 and 30.

In the case of a fracture of the head 81 of the radius 82 of the wrist 80, the groups of pins 60 and 70 are inserted in the radius 82 and in the metacarpus 83 of the index finger 84. The fixation devices 40 and 50 are mounted on the pins and the fixation rods 43 and 53, and the articulated joint 10 is positioned by virtue of the needles 90 making it possible to target the axis of the articulation 80. It is by acting on the assemblies 40 and 50 that the articulated joint 10 can be displaced according to the arrows A and B in FIG. 1.

Referring to FIG. 2, it will be seen that the joint 10 can also be positioned angularly in accordance with the arrow C, that is to say transversely relative to the longitudinal axis of the apparatus.

In FIG. 3 the articulated joint 10 is represented as seen from the side. It consists of a casing 11 in two parts 111 and 112 pressed one against the other by means of screws 12 with heads countersunk in the casing. A screw 13 makes it possible to angularly lock the device 30 permitting the assembly play after positioning it relative to the articulated joint 10 according to the arrow D. The half 111 of the casing comprises an arc-shaped opening 14, centered on the axis 0 of the articulation, and also a scale 15 graduated in degrees. The opening 14 comprises a stop screw 16, integral with a movable rider which will be described later. It will be noticed that the screws 13 and 16 all have the same hexagonal head, so that the adjustments can be carried out with a single tool.

In the arc-shaped opening 14 is the arc-shaped slide 21 which is integral with the device 20 and which has a transverse stud 22 intended to abut, on the one hand, against the front edge of the opening 14 and, on the other hand, against the movable rider integral with the stop screw 16.

The half 112 of the casing additionally comprises two passages for the target needles 91 and 92 used to center the assembly on the 0 axis of the articulation, as will be seen hereinafter.

In FIG. 3 the articulated joint has been shown in its rest position in full lines and in its position of maximum flexion in broken lines. It will be noted that, in the rest position shown by full lines, the rod 43 forms an angle a of about 10° relative to the axis of the device 20 in order to better follow the configuration of the rest position of the wrist. Depending on the particular anatomy of each individual, it is also possible to provide a fixation rod 53 forming a bend of an angle b which may reach about 20°.

The device 20 for transverse adjustment consists of a threaded cylindrical body 23 arranged on the arc-shaped slide 21, which has externally a central opening 24. The rear fixation rod 43 can be displaced axially in the central opening 24 of the cylindrical body 23 according to the arrow E, with the aid of knurled nuts 25 and 26 arranged on either side of the spur 44 at the end of the rod 43.

In the cross-section of the device 20 in FIG. 4 it will be noted that the central opening 24 is extended upwards by a lateral clearance 27 in order to permit orientation of the spur 44 according to the arrow F in FIG. 6. In the variant proposed in the drawing, the connection between the arc-shaped slide 21 and the cylindrical body 23 is achieved by means of a pin 28.

The inner face 17 of each half 111 and 112 of the casing 11 comprises a series of clearances, namely:

a cylindrical clearance 171 for the inner rod 31 of the device 30 permitting play of the assembly;
a hollow 172 for the head 311 of the rod 31, in order to maintain the device 30 in the casing 10;
an arc-shaped clearance 173 in order to permit the passage of the arc-shaped slide 21;
two plane clearances 174, provided on opposite faces, whose use will be referred to hereinafter; and
four openings 175 to 178 intended to receive roller bearings 19 promoting the sliding of the slide 21.

One of the halves 111 or 112 of the casing additionally comprises a tapped opening leading into a clearance 179, which can be seen in FIG. 5, and into which there is screwed the screw 13 permitting angular positioning of the device 30. The screw 13 cooperates with a shoe 18 arranged in the clearance 179. One of the faces of the shoe 18 comprises a cylindrical clearance of a dimension corresponding to the inner rod 31.

Figure 7:
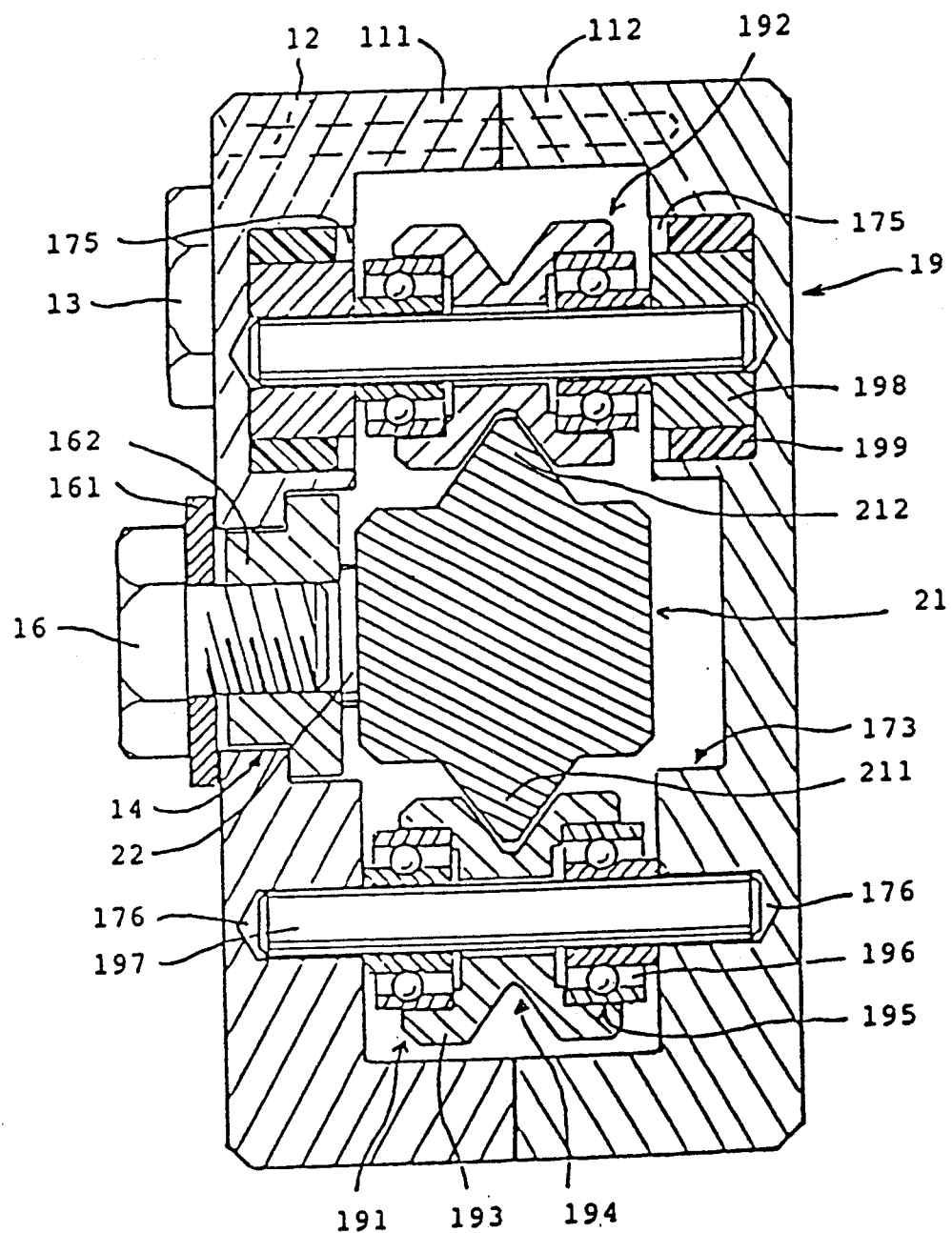
FIG. 7 is a cross-section along VII—VII in FIG. 4, on a larger scale, showing the guide elements of an arc-shaped slide.

The cross-section in FIG. 7 shows the halves 111 and 112 constituting the casing 11 of the articulated joint, and one of the connecting screws 12. It also shows the screw 13 for angular positioning and the stop screw 16 whose head bears on a washer 161 and which is integral with a movable rider 162 arranged inside the arc-shaped opening 14. The movable rider 162 serves as a stop for the transverse stud 22 of the arc-shaped slide 21.

The particular shape of the cross-section of the arc-shaped slide 21 will be noted, the latter comprising two shoulders 211 and 212 of conical cross-section intended to cooperate with roller bearing assemblies 19. It will be noted that the roller bearing assemblies 191 intended to cooperate with the arc-shaped shoulder 211 differ from the roller bearing assemblies 192 intended to cooperate with the arc-shaped shoulder 212.

Each roller bearing assembly 191 comprises a roller 193 comprising a channel 194 of a shape corresponding to the arc-shaped shoulder 211. The faces of the roller 193 comprise clearances 195 intended to receive ball-bearings 196 integral with a central shaft 197.

The roller bearing assembly 192 additionally comprises bearings 198 arranged in the openings 175 and 177 formed in the walls 111 and 112. The bearings 198 are surrounded by an elastomeric seal 199. In a variant this seal may be replaced by a series of 0-rings. The purpose of introducing an elastomeric material is to establish a slight pre-stressing permitting elimination of play.

Referring to FIGS. 8 to 10 showing in detail the components constituting the device 30 permitting play, the inner rod 31 can be seen along with its head 311 intended to hold the assembly relative to the casing 11. Towards the outside, the rod 31 additionally comprises a hollow 312, a shoulder 313 and finishes with a cylindrical part 314. This part 314 comprises a truncated central opening 315 and two opposite lateral clearances 316 (shown in FIGS. 9 and 10) constituting a retention collar 317 intended to provide the connection to the fixation rod 53.

The fixation rod 53 comprises a threaded shoulder 531 and ends with a truncated end 532 of a shape corresponding to that of the central opening 315 of the inner rod 31. The end 532 receives a retention pin 533. A spring 34 (shown partially in broken lines in the drawing) is arranged between the shoulders 531 and 313 and is intended to distance the rods 31 and 53 from one another.

A sleeve 32 is intended to cover the assembly described and comprises, at one end, a tapping 321 intended to cooperate with the threaded shoulder 531 and, at the other end, an inner edge 322 intended to cooperate with the shoulder 313 in order to provide for the compression of the spring 34, this edge delimiting a central opening 323 providing for the passage of the inner rod 31. A silicon seal 534 will advantageously be added as an extension of the shoulder 531, which provides for a braking function in order to prevent untimely loosening of the sleeve 32.

FIGS. 11 and 12 show a variant for positioning the targeting needles 91 and 92 by means of a spring plate 93. The plate 93 comprises two branches 931 and 932 twice folded 90° inwards in such a way that their sides 933 and 934 match the shape of the half of the casing 11 and their ends come into engagement in two plane clearances 174 described with reference to FIG. 4. The plate 93 comprises two lateral arms 935, the opposite edges of which comprise oblique tongues 936 to 939 having an opening for the passage of the needles 91 and 92.

By virtue of the elasticity of the plate 93, it is possible to position it easily on the casing 11 by deformation of the sides 933 and 934 during introduction of the terminal claws of the branches 931 and 932 into the clearances 174. The oblique tongues 936 and 937 are pressed towards each other in order to permit the positioning of the targeting needle 91, in the same way as the tongues 938 and 939 are pressed in order to permit the passage of the needle 92.

The majority of the constituents of the fixation device described are made of stainless steel, only the casing 10 and the arc-shaped slide being of light alloy, in order to reduce the weight of the assembly.

Before being made available to the practitioner, the device is assembled as shown in the drawings.

To this end, the arc-shaped segment 21 is provided with its stop 22 and is made integral, by the pin 27, with the threaded cylindrical body 23 which receives the fixation rod 43, fixed by means of the knurled nuts 25 and 26.

The inner rod 31 of the device 30 and the fixation rod 53 are connected by inserting the retention pin 533 after positioning of the spring 34. The sleeve 32 is then placed over the assembly.

It will be noted that as long as the sleeve is not totally tightened, the rod 31 of the device 30 permitting play and the fixation rod 53 are articulated relative to one another. Indeed, the truncated end 532 is only partially engaged in the truncated opening 315, under the effect of the spring 34 which distances the shoulders 531 and 313 from one another. However, the rods 31 and 53 remain connected at all times, because the retention pin 533 abuts against the collar 317 in the extreme spacing position.

The ends of the pin 533 can be displaced freely in the opposite lateral clearances 316 of the rod 31, and the resulting movement of the sleeve 32 relative to the rod 31 is made possible since its inner edge 322 can be displaced in the hollow 312. It will also be noted that, in addition to the relative articulation of the rods 31 and 53, the proposed construction permits a slight pivoting of the rod 53 relative to the rod 31, a pivoting which is limited as soon as the ends of the retention pin 533 abut on the edges of the clearances 316. As the sleeve 32 is screwed on the threaded shoulder 531, so the relative movement between the rods 31 and 53 decreases.

As has already been mentioned, the silicon seal 534 serves as a brake on the movement of the sleeve 32, in order to prevent its untimely displacement.

To finish the assembly of the fixation device according to the invention, the devices 20 and 30 are positioned in the casing 11. The arc-shaped segment 21 is arranged between the roller bearing assemblies 19 in such a way that the stop 22 projects into the opening 14 between the screw 16 and the front part of the opening. The head 311 for retaining the rod 31 is arranged in the hollow 172, and the shoe 18 is arranged in its clearance 179. The halves 111 and 112 of the casing are then connected by means of screws 12. Provision can be made for covers to be arranged on the heads of the screws 12 in order to prevent the practitioner from actuating them inadvertently.

The device is then ready to be used. At the moment of its positioning, the device is locked in the following manner:

the sleeve 32 is tightened on the threaded shoulder 531, the inner rod 31 is locked angularly in the plane of the apparatus by means of the screw 13 bearing on the shoe 18, the screw 16 and the movable rider 162 are tightened in order to prevent any movement of the arc-shaped slide 21, the nuts 25 and 26 are tightened on both sides of the spur 44, which is arranged longitudinally and angularly in a middle position.

During the operation the practitioner inserts the pins 60 and 70 into the bones, preferably at an angle of about 45° relative to the plane of the hand, then he positions the assemblies 40 and 50 for fixation of the pins. The targeting needles 91 and 92 are then added, and the adjustment of the flanges 42 and 52 permits positioning of the articulated fixation device according to the arrows A and B in FIG. 1, so that the axis of the rotating components corresponds to the axis of the articulation. This adjustment takes place while monitoring the position of the bones by X-ray.

The targeting needles 91 and 92 are removed, as is the plate 93 in the case where use is made of the variant with a removable plate rather than needles passing through openings in the casing.

The practitioner then loosens the screw 13 and one of the knurled nuts 25 or 26, in order to effect the transverse adjustment according to the arrow C in FIG. 2. By moving the patient's hand, after temporarily displacing the screw 16 and its rider 162 in the arc-shaped opening 14, the practitioner achieves automatic positioning of the articulated joint in the transverse plane, then he locks the assembly by means of the screw 13 and the knurled nuts 25 and 26. It should be noted that the latter permit a slight tension to be applied at the level of the fractured bone, in order to achieve decompression of the fracture.

As has already been indicated, the positioning is thus particularly simplified with the type of fixation device described here, since the adjustment in the plane of the arrows A and B in FIG. 1 is independent of the transverse adjustment according to the arrow C in FIG. 2. With the previously known fixation devices, it was necessary to act on the positioning flanges 42 and 52, and there was consequently a risk of disturbing the assembly when a transverse correction was effected.

The assembly remains locked for about 15 days in order for osseous consolidation to begin. Then the screws 16 and its rider 162 are progressively displaced so as to reach, in a few weeks, the maximum flexion movement shown in FIG. 3.

By displacing the knurled nuts 25 and 26 towards the outside, an elongation of the ligaments can be exerted in order to facilitate re-education at the end of treatment.

Moreover, the sleeve 32, which makes it possible to give the device 30 play, can be gradually loosened. The practitioner will carry out this operation depending on the particular anatomy of each patient so that the latter can perform without hindrance the flexion movement permitted by the articulated joint.

We claim:

1. A dynamic external fixation device for osteosynthesis of a fractured joint, comprising:
   (a) a first member (40) having a first fixation rod (43) capable of being connected to pins (60) inserted into a bone on one side of said joint;
   (b) a second member (50) having a second fixation rod (53) capable of being connected to pins (70) inserted into a bone on the other side of said joint;
   (c) an articulating portion (10) connecting said first rod (43) and said second rod (53), said articulating portion (10) comprising a casing (11) having a curved sliding surface with a virtual axis and an arc-shaped segment (21) capable of sliding on said curved sliding surface; and
   (d) means for permitting pivoting of at least one item selected from the group consisting of said first rod (43) and said second rod (53) relative to said casing (11) so as to permit transverse positioning of said articulating portion (10) without affecting the longitudinal adjustment of said articulating portion (10).

2. A fixation device according to claim 1, wherein one end of said arc-shaped segment (21) is integral with a cylindrical body (23) which has an external central opening (24) capable of receiving an end of said first rod (43) and which has a means for fixation of said rod.

3. A fixation device according to claim 2, wherein said central opening (24) comprises a lateral clearance (27) and wherein an end of said rod (43) has a radial spur (44) capable of being displaced longitudinally and radially in said central opening (24) and its lateral clearance (27).

4. A fixation device according to claim 3, wherein said cylindrical body (23) is threaded and wherein a means for fixation of said rod consists of two nuts (25, 26).

5. A fixation device according to claim 1, wherein said second rod (53) is integral with a device which permits play (30) and which is provided with means for fixation to said articulating portion (10) and wherein said articulating portion (10) comprises means for targeting (90) said virtual axis of said sliding surface.

6. A fixation device according to claim 5, wherein said device which permits play (30) comprises an inner rod (31) having one end thereof provided with a head (311) capable of maintaining the assembly in a corresponding clearance (171) in said casing (11) of said articulating portion (10) and having the other end thereof comprising a shoulder (313) and a truncated central opening (315) capable of receiving a corresponding truncated end (532) of said second rod (53), which comprises a threaded shoulder (531) intended to cooperate with a tightening sleeve (32) capable of surrounding said device which permits play (30).

7. A fixation device according to claim 6, wherein said central opening (315) is extended laterally by two opposite clearances (316) constituting a retention collar (317) of an axis (533) which is fixed transversely to an end (532) of said second rod (53).

8. A fixation device according to claim 6, wherein a compression spring (34) is arranged between the shoulder (313) of said inner rod (31) and the shoulder (531) of said second fixation rod (53).

9. A fixation device according to claim 6, wherein said casing (11) comprises means for fixation (13) of said inner rod (31).

10. A fixation device according to claim 1, wherein said casing (11) comprises at least two roller bearing assemblies (191, 192) capable of cooperating with said arc-shaped segment (21), in order to replace sliding action of said arc-shaped segment (21) by rolling action.

11. A fixation device according to claim 10, wherein said arc-shaped segment (21) has in cross-section two opposite conical shoulders (211, 212) each intended to cooperate with a groove (194) of corresponding shape of a roller (193) capable of turning relative to a shaft (197) fixed in said casing (11).

12. A fixation device according to claim 11, wherein ends of said shaft (197) are fixed in recesses (175-178) formed in opposite inner walls of said casing (11).

13. A fixation device according to claim 12, wherein bearings (198) surrounded by an elastomeric seal (199) are inserted between ends of said shaft (197) and said recesses (175-178).

14. A fixation device according to claim 11, wherein ball-bearings (196) are arranged between said roller (193) and said shaft (197).

15. A fixation device according to claim 11, wherein said arc-shaped segment (21) comprises a transverse stop (22) which projects into an arc-shaped opening (14) in said casing (11).

16. A fixation device according to claim 15, wherein an adjustable limitation means (16) is arranged in said arc-shaped opening (14).

17. A fixation device according to claim 1, wherein said casing comprises openings capable of receiving removable targeting means (91, 92).

18. A fixation device according to claim 1, wherein said casing comprises means for fixation of a removable plate (93) which comprises passages for removable targeting means (91, 92).

* * * * *